United States Patent
Somoza et al.

(10) Patent No.: US 11,759,435 B2
(45) Date of Patent: Sep. 19, 2023

(54) DIHYDROCHALCONE DERIVATIVES INFLUENCING INFLAMMATORY STATES

(71) Applicant: SYMRISE AG, Holzminden (DE)

(72) Inventors: Veronika Somoza, Weidling (AT); Katharina Schüller, Vienna (AT); Joachim Hans, Holzminden (DE); Jakob Ley, Holzminden (DE)

(73) Assignee: SYMRISE AG, Holzminden (DE)

( * ) Notice: Subject to any disclaimer, the term of this patent is extended or adjusted under 35 U.S.C. 154(b) by 691 days.

(21) Appl. No.: 16/071,358

(22) PCT Filed: Apr. 28, 2016

(86) PCT No.: PCT/EP2016/059566
§ 371 (c)(1),
(2) Date: Jul. 19, 2018

(87) PCT Pub. No.: WO2017/186298
PCT Pub. Date: Nov. 2, 2017

(65) Prior Publication Data
US 2022/0226261 A1    Jul. 21, 2022

(51) Int. Cl.
| *A61K 31/121* | (2006.01) |
| *A61K 8/35* | (2006.01) |
| *A61Q 11/00* | (2006.01) |
| *A61K 8/42* | (2006.01) |
| *A61K 31/166* | (2006.01) |
| *A61Q 19/00* | (2006.01) |

(52) U.S. Cl.
CPC .............. *A61K 31/121* (2013.01); *A61K 8/35* (2013.01); *A61K 8/42* (2013.01); *A61K 31/166* (2013.01); *A61Q 11/00* (2013.01); *A61Q 19/00* (2013.01)

(58) Field of Classification Search
None
See application file for complete search history.

(56) References Cited

U.S. PATENT DOCUMENTS

| 4,219,569 | A | 8/1980 | Glenn | |
| 8,778,987 | B2 * | 7/2014 | Ley | C07C 49/83 426/538 |
| 8,992,892 | B2 | 3/2015 | Backes et al. | |
| 2010/0183524 | A1 * | 7/2010 | Zielinski | A61P 1/02 424/49 |
| 2011/0189108 | A1 | 8/2011 | Backes et al. | |

FOREIGN PATENT DOCUMENTS

| CN | 1993114 A | 7/2007 |
| DE | 102004041496 A1 | 3/2006 |
| EP | 0613879 A1 | 9/1994 |
| EP | 1972203 A1 | 9/2008 |
| EP | 2353403 A1 | 8/2011 |
| FR | 2942962 A1 | 9/2010 |
| JP | 2003/321351 A | 11/2003 |
| JP | 2004043354 A | 2/2004 |
| JP | 2012102041 A | 5/2012 |
| WO | 2006024587 A1 | 3/2006 |
| WO | 2007089652 A2 | 8/2007 |
| WO | 2010062835 A1 | 6/2010 |
| WO | 2013049507 A1 | 4/2013 |

OTHER PUBLICATIONS

Numerof et al. (Biodrugs 2006; 20 (2): 93-103).*
International Search Report and Written Opinion dated Feb. 13, 2017 in corresponding PCT Application No. PCT/EP2016/059566.
Chinese Office Action dated Aug. 3, 2020 for corresponding Chinese Application No. 201680082579.8.
Jakob P. Ley et al., "Identification of Enterodiol as a Masker for Caffeine Bitterness by Using a Pharmacophore Model Based on Structural Analogues of Homoeriodictyol", Journal of Agricultural and Food Chemistry, vol. 60, No. 25, 2012, pp. 6303-6311.
European Office Action dated May 12, 2020 for corresponding European Application No. 16724297.3.
S.D. Mancini et al., "Cytotoxic Principles from the Sap of Kalmia Latifolia," Journal Of Natural Products, vol. 42, No. 5, 1979, pp. 483-488 XP055687868.
EPO Communication for corresponding European Application No. 16724297.3.
Wen-Chung Huang et al., "Phloretin inhibits interleukin-1B-induced COX-2 and ICAM-1 expression through inhibition of MAPK, Akt, and NF-kBsignaling in human lung epithelial cells," Food and Function, vol. 6, 2015; pp. 1960-1967 XP055336945.
Huang, Wen-Chung et al., "Phloretin and phlorizin promote lipolysis and inhibit inflammation in mouse 3T3-L1 cells and in macrophage-adipocyte co-cultures," Molecular Nutrition & Food Research, vol. 57, 2013, pp. 1803-1813.
Database WPI, Week 201240, Thomson Scientific, London, GB; XP-002766165.
Homma, Masato et al., "Inhibitory Effects of Lignans and Flavonoids in Saiboku-To, a Herbal Medicine for Bronchial Asthma, on the Release of Leukotrienes from Human Polymorphonuclear Leukocytes," Planta Medica, vol. 66, No. 1, 2000, pp. 88-91.
Waisser, Karel et al., "On the Relationship between the Structure and Antimycobacterial Activity of Substituted N-Benzylsalicylamides," Collection Symposium Series (XIIIth Symposium on Chemistry of Nucleic Acid Components Spindleruv Mlyn, Czech Republic); vol. 68, No. 7, 2003, pp. 1275-1294.
Cho, Sung Jin et al., "N-Benzylbenzamides: A new class of potent tyrosinase inhibitors," Bioorganic & Medicinal Chemistry Letters, vol. 16, 2006, pp. 2682-2684.
Philippines Office Action dated Mar. 31, 2023 for corresponding Philippines Application No. 1/2018/501804.

* cited by examiner

Primary Examiner — Bong-Sook Baek
(74) Attorney, Agent, or Firm — POLSINELLI PC

(57) ABSTRACT

The present invention belongs to the area of pharmaceutical and cosmetic compositions and refers to compounds, novel mixtures and preparations comprising certain compound(s) of formula (I) which show anti-inflammatory properties.

2 Claims, No Drawings

US 11,759,435 B2

DIHYDROCHALCONE DERIVATIVES INFLUENCING INFLAMMATORY STATES

CROSS-REFERENCE TO RELATED APPLICATIONS

This application is a national stage application (under 35 U.S.C. § 371) of PCT/EP2016/059566, filed Apr. 28, 2016, which is incorporated herein by reference in its entirety.

FIELD OF INVENTION

The present invention belongs to the area of pharmaceutical and cosmetic compositions and refers to compounds, novel mixtures and preparations comprising certain compound(s) of formula (I) which show anti-inflammatory properties.

STATE OF THE ART

There is a constant need to provide inflammation-inhibiting substances for the protection of cells or tissues (of people and animals), in particular of the skin of lips, mouth and throat, above all for use in cosmetic preparations, pharmaceutical preparations, food and beverage preparations (oral consumables). In particular there is a constant need to find new substances with anti-inflammatory activities which support the natural defence mechanisms against inflammation in physiological systems (of people and animals). In this respect, there is particularly great interest in substances which are based on naturally occurring scaffolds, particularly attractive for use in foods are substances, which are used or are elected to be used as flavouring compounds and are therefore already evaluated for safe human or animal use.

Accordingly, in the context of the present text, the term "skin" comprises surface and glandular epithelia, i.e. in particular also mucous membranes of the lips, the oral cavity, the throat, the gastric mucosa and the intestinal mucosa. As barrier organs of the (human) body, the mucous membranes are exposed to external influences to a particular extent. They line the various body cavities which are either in contact with the external environment (e.g. mouth and throat) or the internal organs of a body (e.g. intestinal lumen).

Many intrinsic factors (e.g. genetic predisposition) and extrinsic factors (e.g. damage to the skin barrier, influence of bacteria, viruses, fungi, other infections, chemicals, autoimmune reactions, skin-irritant or allergy-triggering substances) can lead to skin irritation or dysfunctions of the skin.

Skin inflammation can in particular also concern or comprise irritation of the mucous membranes in the oral cavity, for example periodontitis and gingivitis (as described in detail below), irritation and infections such as pharyngitis/tonsillitis, and irritation of the gastrointestinal tract, e.g. stomach inflammation and abzesses, irritable bowel disease, Crohns disease, colitis ulcerosa, other colitis types etc.

Periodontal diseases are a worldwide health problem with a high prevalence and incidence (Petersen, P. E., *The World Oral Health Report* 2003: *Continuous improvement of oral health in the* 21*st century—The approach of the WHO Global Oral Health Programme*. Community Dentistry and Oral Epidemiology, 2003. 31(SUPPL. 1): p. 3-24). In 2005, 50-90% of the world population suffered from mild to severe forms of periodontal diseases and the majority of adults especially in industrialized countries suffer from gingivitis, the mildest and most abundant form of oral disease. The human gingiva mainly consists of epithelial cells and gingival fibroblasts, which produce connective tissue components. As part of the immune response to bacterial challenges (mainly by *Porphyromonas gingivalis, Bacteroides forsythus* and *Actinobacillus actinomycetemcomitans*), gingival cells release cytokines and chemokines, among those interleukin 8 (IL-8). In healthy gum tissues the immune response to bacterial challenge is delicately balanced. Cytokines and chemokines, especially IL-8, regulate recruitment, migration, proliferation and differentiation of immune and non-immune cells, synthesis and degradation of tissue matrix and the constant turnover of immune cells resulting in elimination of pathogenic microorganisms thus maintaining tissue integrity. The abstention from any kind of oral hygiene, resulting in formation of bacterial plaque on the exposed tooth surface, leads to acute inflammation of gingival tissue within 21 days. If un-treated, over-activation of the immune response causes persistent activation of destructive mediator pathways, leading to attachment loss, formation of periodontal pockets and in the worst case alveolar bone destruction and tooth. Common prevention strategies include regular tooth-brushing, the use of dental floss and antimicrobial mouthwashes, but also the supplementation of oral health products with anti-inflammatory compounds, to attenuate inflammation on a daily basis.

Darveau, R. P., *Periodontitis: a polymicrobial disruption of host homeostasis*. Nat Rev Microbiol, 2010. 8(7): p. 481-90 describes the interaction of host immune system with oral bacteria in healthy states and in diseased states. Further disclosed is that periodontitis is a bacterially induced chronic inflammatory disease of the periodontium.

Dentino, A., et al., *Principles of periodontology*. Periodontology 2000, 2013. 61(1): p. 16-53 established that dental biofilm ("plaque") consisting of many microbial species and their products is an etiological agent of periodontal disease.

In Maruyama T. et al., *Supplementation of green tea catechins in dentrifrices suppresses gingival oxidative stress and periodontal inflammation*, Achives of Oral Biology 56 (2011), 48-53, is reveal that adding green tea catechins to a dentrifrice may contribute to prevention of periodontal inflammation by decreasing gingival oxidative stress and expression of cytokins.

In McClanahan, S. F. and R. D. Bartizek, *Effects of Triclosan/Copolymer Dentifrice on Dental Plaque and Gingivitis in a* 3-*Month Randomized Controlled Clinical Trial: Influence of Baseline Gingivitis on Observed Efficacy*. Journal of Clinical Dentistry, 2002. 13(4): p. 167-178, studies have been performed about triclosan/pyrophosphate dentrifrice, which show efficacy against dental plaque but not gingivitis. Further, experimental gingivitis studies on triclosan and in combination with other dentrifrice ingredients demonstrate only moderate antimicrobial activity.

However, in addition to bacteria, chemical or mechanical damage can also cause irritation or inflammatory reactions of the gum or the oral mucosa. Pro-inflammatory mediators, in particular interleukins such as IL-1 alpha and PGE2, are released in this process.

There are essentially two enzymatic pathways for regulating inflammation. The lipoxygenase pathway (5-LOX) results in the production of leukotrienes, which have a pro-inflammatory action. The second pathway is the cyclooxygenase pathway (COX-1 and COX-2). A high level of COX-2 indicates inflammation. Further inflammation markers are tumour necrosis factor (TNF-α), nuclear factor κB (NF-κB), interleukin-6 (IL-6), interleukin-8 (IL-8), interleukin-17 (IL-17) and interleukin-1-β (IL1-β). The enzymes, cytokines and metabolites thereof increase the production of prostaglandins and leukotrienes, which function as intercellular mediators, and are connected with the inflammatory process. Regulation of the enzymes LOX-5 and COX-2 in particular can have a positive effect in the development/suppression of inflammation.

Object of the present invention was therefore to provide novel compounds and mixtures thereof, which are suitable for use in the prophylaxis and/or treatment of inflammation and/or inflammatory disease, preferably of diseases and symptoms that are concerned with inflammation as described beforehand. Particularly, it was the object of the invention to provide novel compounds and mixtures thereof, which especially show efficacy against skin irritation and inflammation diseases. An important object was further he focus on chronic inflammatory diseases of the periodontium.

DESCRIPTION OF THE INVENTION

Object of the present invention is a compound of formula (I) or any salt of a compound of the formula (I)

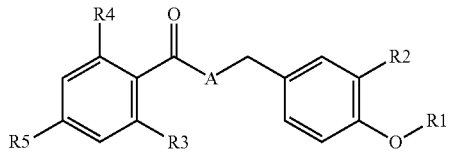

(I)

wherein R1 represents hydrogen, methyl, ethyl, 1-propyl, 2-propyl, 1-butyl, 2-butyl- or 2-methylprop-2-yl, R2 represents hydrogen, hydroxyl or methoxy, ethoxy, 1-propoxy, 2-propoxy, 1-butoxy, 2-butoxy- or 2-methylprop-2-oxy; and A is —NH— or —CH$_2$—; and wherein in case A is —NH— at least one of the residue R3, R4, R5 is a hydroxyl and the other two residues R3, R4, R5 are independently of one another and are selected from the group consisting of hydroxy or hydrogen; and
wherein in case A is —CH$_2$— at least two of the residues R3, R4 or R5 is a hydroxyl, and one of the residues R3, R4, R5 is a hydroxyl or hydrogen,
for use in the prophylaxis and/or treatment of inflammation and/or inflammatory disease.

In a preferred embodiment of the present invention the compound of formula (I) is a compound of formula (Ia) and/or (Ib), or a salt thereof:

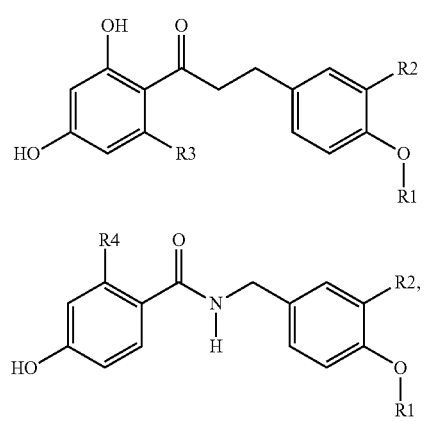

wherein R1 represents hydrogen, methyl, ethyl, 1-propyl, 2-propyl, 1-butyl, 2-butyl- or 2-methylprop-2-yl, R2 represents hydrogen, hydroxyl or methoxy, ethoxy, 1-propoxy, 2-propoxy, 1-butoxy, 2-butoxy- or 2-methylprop-2-oxy; and R3 in formula (Ia) is hydrogen or hydroxyl, and R4 in formula (Ib) is hydrogen or hydroxyl.

In a more preferred embodiment of the present invention the compound of formula (Ia) is selected from a compound of formula (Ia') or (Ia").

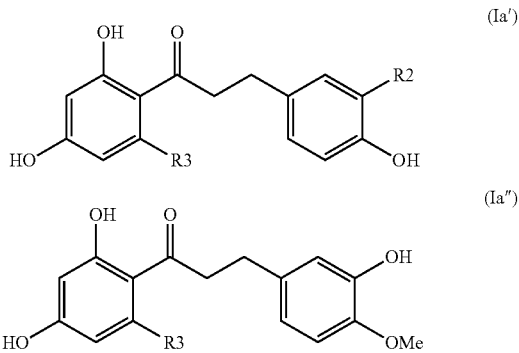

or a mixtures of (Ia') and (Ia"), wherein R3 is hydrogen or hydroxyl.

In another preferred embodiment of the present invention the compound of formula (Ib) is preferably the compound of formula (Ib') or a salt thereof:

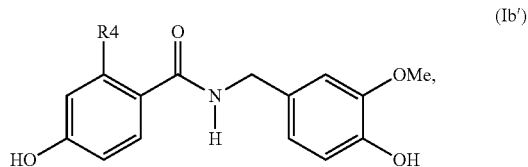

wherein R3 is hydrogen or hydroxyl.

Preferred compound(s) of formula (I), respectively formula (Ia), (Ib), (Ia'), (Ia") and (Ib') is/are selected from the group consisting of:

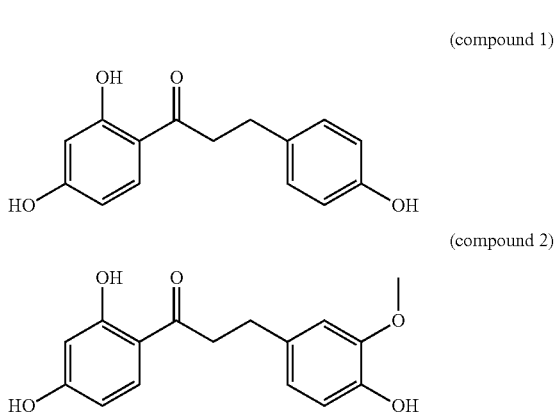

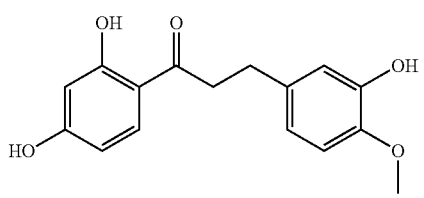
(compound 3)

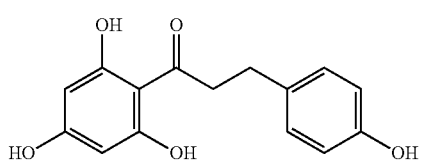
(compound 4)

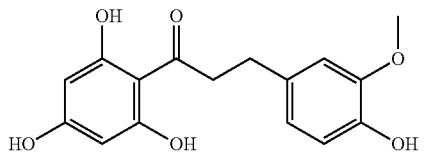
(compound 5)

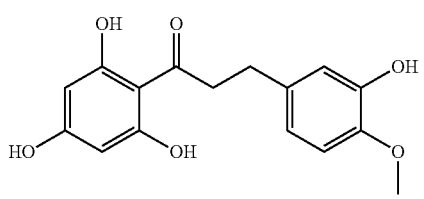
(compound 6)

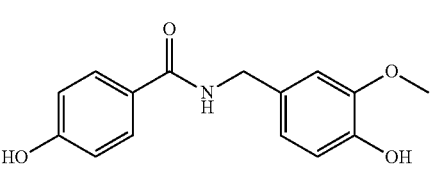
(compound 7)

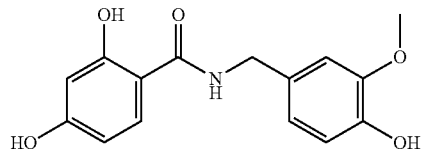
(compound 8)

Surprisingly, it has been observed that the described compounds, salts and mixtures thereof show excellent anti-inflammatory properties.

In general, the present invention relates to the aforementioned compounds of formula (I), respectively formula (Ia), (Ib), (Ia'), (Ia") and (Ib'), salts or mixtures thereof as anti-inflammatory active substances. In preferred embodiment the present invention relates to the aforementioned compounds 1 to 8 salts or mixtures thereof as anti-inflammatory active substances.

For salts of compounds of the formula (I), respectively formula (Ia), (Ib), (Ia'), (Ia") and (Ib'), usable according to the invention, that stated further above respectively applies as regards the preferable meanings of the residues. One or more hydroxy are optionally also present deprotonated. Here, as well as the deprotonated compound(s) of the formula (I), a corresponding quantity of counter-cations are present, where these are preferably selected from the group consisting of: singly positively charged cations of the first main and transition group, ammonium ions, trialkylammonium ions, doubly positively charged cations of the second main and transition group and triply positively charged cations of the third main and transition group, and mixtures thereof. The maximum degree of deprotonation of a com-pound of the formula (I), respectively formula (Ia), (Ib), (Ia'), (Ia") and (Ib'), on which such as salt is based is found from the carboxyl group and the hydroxy groups of this compound lying adjacent thereto. In turn, from the number of deprotonated groups, the corresponding number of counter-cations is obtained (depending on their charge). Thus for example for a com-pound of the formula (I) with one carboxyl and one hydroxy group on which such as salt is based, it is found that with complete deprotonation of the groups a doubly negatively charged anion is present, from which in turn the number of positive charges is found (here: two), which must be provided by the counter-cation(s). Particularly preferably, these counter-cations are cations selected from the group consisting of Na+, K+, NH4+, Ca2+, Mg2+, Al3+ and Zn2+.

Compound derivatives of formula (I) are known as flavour compounds: Compounds 1, 2, 4, and 5 were described as flavour compounds exhibiting masking activities against off-taste causing food constituents in EP 1,972,203; compound 6 is also known from the literature and is described, inter alia, in J. Agric. Food Chem. 1977, 25(4), 763-772, as a sweet-tasting substance, compound 3 was claimed to increase sweetness in calorie reduced formulations in EP 2,353,403; compounds 7 and 8 were described as bitter-masking flavour compounds in EP 1,784,088.

The compounds of formula (I), respectively formula (Ia), (Ib), (Ia'), (Ia") and (Ib') and specifically compounds (1) to (8) described herein, advantageously possess a particularly strong anti-inflammatory action. The compounds of formula (I), respectively formula (Ia), (Ib), (Ia'), (Ia") and (Ib') and specifically (1) to (8) are advantageously suitable for supporting the natural defence mechanisms against inflammatory processes in physiological systems (of people and animals).

Preferably a preparation in the sense of the present invention comprises one, two, three, four, five, six, seven, of compounds of formula (I), respectively formula (Ia), (Ib), (Ia'), (Ia") and/or (Ib'), more preferably advantageous the preparation comprises at least two compounds of formula (I), respectively formula (Ia), (Ib), (Ia'), (Ia") and/or (Ib') and specifically compounds (1) to (8). Most preferred is a preparation in which one, two, three, four, five, six, seven or all compounds (1) to (8). are present in the preparation.

An important aspect of the present invention is therefore a compound of formula (I), respectively formula (Ia), (Ib), (Ia'), (Ia") and (Ib'), salts or mixtures thereof as defined above for use in the prophylaxis and/or treatment of inflammation and/or inflammatory disease.

Another important aspect of the present invention is a compound of formula (I), respectively formula (Ia), (Ib), (Ia'), (Ia") and (Ib'), salts or mixtures thereof as defined above for use in the prophylaxis and/or treatment of diseases associated with the release
a) of TNF-alpha, and/or
b) of an interleukin, preferably of IL-1, IL-6 and/or IL-8, and/or
c) of a prostaglandin, preferably of PGE2, and/or
d) of interferon-gamma and/or NF-κB.

Preference is hereby also made to a cosmetic use of a compound of formula (I), respectively formula (Ia), (Ib), (Ia'), (Ia") and (Ib'), salts or mixtures thereof as defined above for use in the prophylaxis and/or treatment of diseases associated with y the release
a) of TNF-alpha, and/or
b) of an interleukin, preferably of IL-1, IL-6 and/or IL-8, and/or
c) of a prostaglandin, preferably of PGE2, and/or
d) of interferon-gamma and/or NF-κB.

Another aspect of the present invention is a pharmaceutical or cosmetic preparation containing at least one compound of formula (I), respectively formula (Ia), (Ib), (Ia'), (Ia") and (Ib') as defined above or a pharmaceutically or cosmetically acceptable salt of a compound of formula (I), respectively formula (Ia), (Ib), (Ia'), (Ia") and (Ib') containing two or more of these compounds or the salts thereof for use in the prophylaxis and/or treatment of inflammation.

A further object of the invention is a pharmaceutical or cosmetic preparation containing at least one compound of formula (I), respectively formula (Ia), (Ib), (Ia'), (Ia") and (Ib') as defined above or a pharmaceutically or cosmetically acceptable salt of a compound of formula (I), respectively formula (Ia), (Ib), (Ia'), (Ia") and (Ib') a mixture containing two or more of these compounds or the salts thereof for use in the prophylaxis and/or treatment of diseases associated with the release
a) of TNF-alpha, and/or
b) of an interleukin, preferably of IL-1, IL-6 and/or IL-8, and/or
c) of a prostaglandin, preferably of PGE2, and/or
d) of interferon-gamma and/or NF-κB.

It was particularly surprising that the compounds of the formula (I), respectively formula (Ia), (Ib), (Ia'), (Ia") and (Ib') and specifically compounds (1) to (8) to be used according to the invention or salts thereof can mediate or possess strong anti-inflammatory effects. Compounds, salts, mixtures and preparations according to the invention, as described herein, are advantageously capable of positively influencing inflammatory parameters in monocytes. In cell models wherein irritated and inflammatory phenomena of the mucous membranes, especially of gingiva and the gastrointestinal tract, are simulated, these exhibit an anti-inflammatory action. In particular, the following inflammatory parameters are positively influenced according to the invention: PGE2, IL-1, TNF, IL-6 and IL 8, in particular PGE2. Appropriate experiments on this were performed as described in TS1 (see below, "Example TS: Test study"). Thus for example from a concentration of 0.2 µg/l, substances according to formula (I), respectively formula (Ia), (Ib), (Ia'), (Ia") and (Ib') and specifically compounds (1) to (8) already exhibit a highly significant action on some of the abovementioned parameters. Concentrations of 20 µg/l and more are particularly suitable.

Particularly preference is therefore made to a pharmaceutical or cosmetic preparation comprising at least one compound of formula (I), respectively formula (Ia), (Ib), (Ia'), (Ia") and (Ib') as defined above or a pharmaceutically or cosmetically acceptable salt of a compound of formula (I), respectively formula (Ia), (Ib), (Ia'), (Ia") and (Ib') or a mixture containing two or more of these compounds or the salts thereof and a pharmaceutically or cosmetically acceptable carrier, solvents, adjuvants or diluents.

A further aspect of the present invention is an oral composition for use in the treatment, inhibition or reduction of an oral inflammatory condition comprising: at least one compound of formula (I), respectively formula (Ia), (Ib), (Ia'), (Ia") and (Ib') as defined above or a pharmaceutically or cosmetically acceptable salt of a compound of formula (I), respectively formula (Ia), (Ib), (Ia'), (Ia") and (Ib') or a mixture containing two or more of these compounds or the salts thereof and a pharmaceutically or cosmetically acceptable carrier, solvents, adjuvants or diluents.

According to a preferable embodiment of the present invention, the proportion of the total quantity of compounds of the formula (I)), respectively formula (Ia), (Ib), (Ia'), (Ia") and (Ib') and salts thereof in the (cosmetic or pharmaceutical) preparation lies in the range from 0.1 ppm to 120 ppm, preferably in the range from 0.1 ppm to 60 ppm, particularly preferably in the range from 0.1 ppm to 30 ppm, based on the total amount of all compounds of formula (I),), respectively formula (Ia), (Ib), (Ia'), (Ia") and (Ib') referring to the total amount of the preparation.

Preferably the use of a compound of formula (I), respectively formula (Ia), (Ib), (Ia'), (Ia") and (Ib') for the manufacture of a pharmaceutical or cosmetic preparation for the prophylaxis and/or treatment of inflammation and/or inflammatory disease is more preferably for reducing the release
a) of TNF-alpha, and/or
b) of an interleukin, preferably of IL-1, IL-6 and/or IL-8, and/or
c) of a prostaglandin, preferably of PGE2, and/or
d) of interferon-gamma and/or NF-κB.

Advantageously, it has been shown that the compounds of the present invention possess an excellent character in reducing the release of said factors a) to d) and thus contribute to the prophylaxis and/or treatment of inflammation and/or inflammatory disease.

In a preferred embodiment the use of a compound of formula (I) is for the manufacture of a pharmaceutical or cosmetic preparation for
a) strengthening damaged or undamaged skin, in particular oral mucosa,
b) recreating or stabilizing the function of skin, in particular of oral mucosa,
c) reducing tissue damage, in particular tissue damage in the intestine,
d) recreating a normal cellular composition in the intestine.

Advantageously, it has been shown that the compounds of the present invention possess properties a) to d) in preparations and thus contribute to the prophylaxis and/or treatment of inflammation and/or inflammatory disease.

Preference is made to the use of the present invention for the prophylaxis or treatment of inflammation or inflammatory diseases, wherein said inflammatory diseases is preferably from chronic inflammatory diseases, in particular skin or oral inflammatory diseases, preferably oral inflammatory diseases.

"Therapeutically effective amount" is intended to include an amount of a compound of the present invention alone or an amount of the combination of compounds claimed or an amount of a compound of the present invention in combination with other active ingredients effective to inhibit or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The phrase "pharmaceutically or cosmetically acceptable" is employed herein to refer to those compounds, materials, compositions, and/or dosage forms which are, within the scope of sound medical or cosmetic judgment, suitable for use in contact with the tissues of human beings and animals without excessive toxicity, irritation, allergic response, or other problem or complication, commensurate with a reasonable benefit/risk ratio.

As used herein, "pharmaceutically or cosmetically acceptable salts" refer to derivatives of the disclosed compounds wherein the parent compound is modified by making acid or base salts thereof. Examples of pharmaceutically or cosmetically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

A further aspect of the present invention is a process for inhibiting and/or relieving a skin inflammation in a subject in need thereof, comprising applying a preparation to an area of the subject's skin to be treated, wherein said preparation comprises the compound of formula (I), respectively formula (Ia), (Ib), (Ia'), (Ia") and (Ib') in a sufficient effective amount to inhibit and/or relieve the skin inflammation and/or in a effective amount to reduce the release of an interleukin, preferably IL-1, IL-6 and/or IL-8, more preferably IL-8, wherein the preparation further comprises acceptable carriers, diluents, excipients or adjuvants.

Preference is made here to a preparation comprising at least one compound, more preferably two, three or more compounds of formula (I), respectively formula (Ia), (Ib), (Ia'), (Ia") and (Ib'), most preferred specifically one, two, three, four five, six, seven or all compounds (1) to (8), and acceptable carriers, diluents, excipients or adjuvants.

A further aspect of the present invention is a process for reducing the release of an interleukin in a subject in need thereof, comprising applying a preparation to an area of the subject's skin to be treated, wherein said preparation comprises the compound of formula (I) in a sufficient concentration to reduce the release of the interleukin and/or to relieve a skin irritation and/or a skin inflammation, wherein the interleukin is preferably IL-8, and the preparation further comprises acceptable carriers, diluents, excipients or adjuvants.

Another further object of the present invention is a method for the prophylaxis and/or treatment of inflammation comprising administering a compound of formula (I), or a salt or a mixture thereof:

The method of the present invention preferably is at least one of a) prophylaxis and/or treatment of inflammation of the skin,
b) reducing the release of TNF-alpha,
b) reducing the release of an interleukin, preferably of IL-1, IL-6 and/or IL-8,
c) reducing the release of a prostaglandin, preferably of PGE2, and/or
d) reducing the release of interferon-gamma and/or NF-κB.

Preferably the method of the present invention for prophylaxis and/or treatment of inflammation, preferably comprises
a) a method for the prophylaxis and/or treatment of chronic inflammatory diseases, and/or
b) a method for reducing tissue damage, in particular tissue damage in the intestine, and/or
c) a method for recreating a normal cellular composition in the intestine, and/or
d) a method for strengthening damaged or undamaged skin, in particular oral mucosa, and/or
e) a method for recreating or stabilizing the function of skin, in particular of oral mucosa.

Preparations according to the invention (in particular the preparations designated above as preferable) are preferably food supplements, medicinal products and pharmaceutical products selected from the group consisting of:

Confectionery is in particular lozenges and chewing gums, fruit gums, chewing sweets, (breath freshening) sweets, boiled sweets, hard caramels, chocolate creams, sweets and chocolate.

Instant products are in particular instant meals and other instant products, e.g. drink powders and granules.

Further preferable preparations, in particular food supplements, medicinal products and pharmaceutical products, are Solid galenical forms (such as for example tablets (with and without coating, with and without modified release), sugar-coated tablets (with and without coating, with and without modified release), capsules (soft or hard gelatine capsules with and without modified release) granules (with and without modified release), powders (with and without modified release), suppositories (with and without coating, with and without modified release), lozenges and chewing gums), Liquid forms (such as for example solutions, suspensions, emulsions, syrups (colloquially cough syrup), mouthwashes, gargle solutions, throat sprays or nasal sprays, nasal drops, nasal rinse solutions, nasal powders, nasal ointments or ear drops, ear sprays, ear rinse solutions, ear powders and aural tampons), Semisolid forms (such as for example hydrophobic ointments including for example: hydrocarbon gels, lipogels, sili cone gels, oleogels and water-absorbing ointments including for example absorption bases, hydrophilic ointments, hydrophilic gels (hydrogels) or pastes, Oral care products (e.g. toothpaste, tooth cream, tooth gel, tooth powder, tooth cleaning fluid or foam, mouthwash, tooth cream and mouthwash as 2-in-1 product, mouth spray, dental floss or dental care chewing gum). Such oral or dental care products as a rule contain abrasive systems (abrasive or polishing ingredients), such as silicates, calcium carbonate, calcium phosphate, aluminium oxide and/or hydroxyapatite, surfactant substances, e.g. sodium laurylsulphate, sodium laurylsarcosinate and/or cocamidopropyl betaine, humectants such as glycerol and/or sorbitol, thickeners, e.g. carboxymethyl-celluloses, polyethylene glycols, carrageenan and/or Laponite®, sweeteners such as saccharin, flavour/taste correctants for unpleasant taste sensations, taste-modulating substances (e.g. inositol phosphate, nucleotides, e.g. guanosine monophosphate, adenosine monophosphate or other substances, e.g. sodium glutamate or 2-phenoxy-propionic acid), cooling active substances, e.g. menthol derivatives (e.g. L-menthyl lactate, L-menthyl alkyl carbonates, menthone ketals), icilin and icilin derivatives, stabilizers and active substances, e.g. sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium lactate, potassium citrate, potassium nitrate, potassium chloride, strontium chloride, hydrogen peroxide, flavourings, sodium bicarbonate and/or odour correctants, and Chewing gums or dental care gums consisting of a chewing gum base containing elastomers, e.g. polyvinyl acetates (PVA), polyethylenes, (low or medium molecular weight) polyisobutenes (PIB), polybutadienes, isobutene-isoprene copolymers, polyvinyl ethyl ethers (PVE), polyvinyl butyl ethers, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate, and mixtures of the said elastomers such as for example described in EP 0 242 325, U.S. Pat. Nos. 4,518,615, 5,093,136, 5,266,336 5,601, 858 or 6,986,709. In addition, chewing gum bases contain further ingredients, e.g. (mineral) fillers (e.g. calcium carbonate, titanium dioxide, silicon dioxide, talc, aluminium oxide, dicalcium phosphate, tricalcium phosphate, magnesium hydroxide and mixtures thereof, plasticizers (e.g. lanolin, stearic acid, sodium stearate, ethyl acetate, diacetin (glycerol diacetate), triacetin (glycerol triacetate) and triethyl citrate), emulsifiers (e.g. phosphatides, such as lecithin and mono and diglycerides of fatty acids, e.g. glycerol monostearate), antioxidants, waxes (e.g. paraffin waxes, candelilla waxes, carnauba wax, microcrystalline waxes and polyethylene waxes), fats or fatty oils (e.g. hardened (hydrogenated) plant or animal fats) and mono, di- or triglycerides.

Preferable preparations according to the invention used for food or enjoyment are:

Confectionery such as for example lozenges and chewing gums, fruit gums, chewing sweets, (breath freshening) sweets, boiled sweets, hard caramels, chocolate creams, sweets and chocolate, bakery products such as cakes, waffles and biscuits, snacks, instant meals and other instant products (drink powders and granules), ice cream, fruit preparations (jams, preserves and fruit sauces), desserts (puddings, jellies), dairy products (quark, yoghurts, probiotic yoghurts, milk drinks, whey preparations) and cereals (cornflakes, muesli and muesli bars).

Particularly preferred is the pharmaceutical or cosmetic preparation of the present invention for oral or topical use, in case of topical, preferably for skin.

Preferably is a pharmaceutical or cosmetic preparation of the present invention an oral composition selected from (hard) candies, compressed tablets, capsules, pills, pastilles, chewing gums, toothpastes and mouth washes.

Additives For the Preparations

As further components for preparations according to the invention used in particular for food or enjoyment, normal primary, auxiliary and additive substances for food or luxury consumables can be used, e.g. water, mixtures of fresh or processed, plant or animal primary or raw substances (e.g. raw, roast, dried, fermented, smoked and/or boiled meat, bones, cartilage, fish, vegetables, fruit, spices, nuts, vegetable or fruit juices or pastes or mixtures thereof), digestible or non-digestible carbohydrates (e.g. amylose, amylopectin, inulin, xylans, cellulose), natural or hardened fats (e.g. tallow, lard, palm fat, coconut fat, hardened plant fat), oils (e.g. sunflower oil, peanut oil, maize oil, olive oil, fish oil, soya oil, sesame oil), fatty acids or salts thereof (e.g. potassium stearate), proteinogenic or non-proteinogenic amino acids and related compounds (e.g. ☒-amino-butyric acid, taurine), peptides (e.g. glutathione), native or processed proteins (e.g. gelatine), enzymes (e.g. peptidases), nucleic acids, nucleotides, taste correctants for unpleasant taste sensations, further taste modulators for further, as a rule not unpleasant taste sensations, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum Arabic), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidulants (e.g. malic acid, acetic acid, citric acid, tartaric acid, phosphoric acid), bitter substances (e.g. quinine, caffeine, limonin, amarogentin, humolone, lupolone, catechins, tannins), mineral salts (e.g. sodium chloride, potassium chloride, magnesium chloride, sodium phosphate), substances preventing enzymatic browning (e.g. sulphite, ascorbic acid), essential oils, plant extracts, natural or synthetic dyes or pigments (e.g. carotenoids, flavonoids, anthocyans, chlorophyll and derivatives thereof), spices, trigeminally active substances or plant extracts, containing such trigeminally active substances, cooling active substances such as for example menthol, menthol derivatives (e.g. L-menthol, L-menthyl lactate, L-menthyl glutarate, L-menthyl succinate) or cubebol, synthetic, natural or nature-identical flavourings or aromatic substances and odour correctants.

Preparations according to the invention, used in particular for food or enjoyment can additionally contain one or more taste correctants, preferably selected from the following list: glutamic acid and its salts e.g. monosodium glutamate, mono potassium glutamate, nucleotides (e.g. adenosine 5'-monophosphate, cytidine 5'-monophosphate) or pharmaceutically acceptable salts thereof, lactisols, sodium salts (e.g. sodium chloride, sodium lactate, sodium citrate, sodium acetate, sodium gluconate), hydroxy-flavanones (e.g. eriodictyol, naringenin, homoeriodictyol or sodium salts thereof), in particular according to US 2002/0188019, amino acids (e.g. gamma-aminobutyric acid as per WO 2005/096841 for reduction or masking of an unpleasant taste sensation such as bitterness), malic acid glycosides as per WO 2006/003107, Strombines, Theogallines according to JP 2007 110988 A, cinnamic acid amides according to EP 2,529,632-B1 or WO 2013 000,673), hesperitine according to EP 1909599 A1, phloretin according to EP 1972203 B1 or EP 1998636 B1, hydroxyflavanes according to US 2010 292175 AA, 4-hydroxychalcones according to EP 1972203 B1, extracs based on Hydrangea dulcis according to EP 2298084 A2, extracts based on Rubus suavissimus according to EP 2,386,211 or WO 2015 189,346, Rubemamin oder Rubescenamin nach EP 2,529,632-B1, neoflavonoids according to EP 2,570,036, EP 2,725,026 or EP 2,570,035, extracts and isolated Balansins from Mycetia balansae according to WO 2012 164,062, saponins according to EP 2,559,346, vanillyllignans such as matairesinol according to EP 2,517,574, salty-tasting mixtures as per WO 2007/045566.

Preparations according to the invention used in particular for food or enjoyment can addi-tionally contain one or more alkamides, preferably selected from the group consisting of: 2E,4E-decadienoic acid N-isobutylamide (pellitorin), 2E,4Z-decadienoic acid N-isobutylamide (cis-pellitorin), 2Z,4Z-decadienoic acid N-isobutylamide, 2Z,4E-decadienoic acid N-isobutylamide, 2E,4E-decadienoic acid N-([2S]-2-methylbutyl)amide, 2E,4E-decadienoic acid N-([2S]-2-methylbutyl)amide, 2E,4E-decadienoic acid N-([2R]-2-methylbutylamide), 2E,4Z-decadienoic acid N-(2-methylbutyl)amide, 2E,4E-decadienoic acid N-piperide (achilleamide), 2E,4E-decadienoic acid N-piperide (sarmentin), 2E-decenoic acid N-isobutylamide, 3E-decenoic acid N-isobutylamide, 3E-nonenoic acid N-isobutylamide, 2E,6Z,8E-decatrienoic acid N-isobutylamide (spilanthol), 2E,6Z,8E-decatrienoic acid N-([2S]-2-methylbutyl) amide (homospilanthol), 2E,6Z,8E-decatrienoic acid N-([2R]-2-methylbutyl)amide, 2E-decen-4-ynic acid N-isobutylamide, 2Z-decen-4-ynic acid N-isobutylamide, sanshoole.

Preparations according to the invention, used in particular for prophylaxis and supplementation of food and for the therapy of disease states and for toiletries can preferably contain substances or combinations of substances from the following groups.

Fillers (e.g. cellulose, calcium carbonate), free-flow and anticaking agents (e.g. talc, magnesium stearate), coatings (e.g. polyvinyl acetate phthalate, hydroxypropyl-methylcellulose phthalate), disintegrants (e.g. starch, crosslinked polyvinylpyrrolidone), plasticizers (e.g. tri-ethyl citrate, dibutyl phthalate) substances for granulation (lactose, gelatine), retardation (e.g. poly(meth)acrylic acid methyl/ethyl/ 2-trimethylaminoethyl ester copolymers in dispersion, vinyl acetate/crotonic acid copolymers) and compacting (e.g. micro-crystalline cellulose, lactose), solvent, suspension or dispersion agents (e.g. water, ethanol), emulsifiers (e.g. cetyl alcohol, lecithin), substances for modification of the rheological properties (silicon dioxide, sodium alginate), substances for microbial stabilization (e.g. benzalkonium chloride, potassium sorbate), preservatives and antioxidants (e.g. DL-alphatocopherol, ascorbic acid), substances for modification of the pH (lactic acid, citric acid), propellant or inert gases (e.g. fluorinated chlorohydrocarbons, carbon dioxide), colorants (iron oxides, titanium dioxide), ointment bases (e.g. paraffins, beeswax), inter alia as described in the technical literature (e.g. Schmidt, Christin. Active and Auxiliary Substances for Individual and Bulk Formulation, and Large-scale Manufacture. 1999; Wissenschaftliche Verlagsgesellschaft mbH Stuttgart or Bauer, Frömming Führer. Textbook of Pharmaceutical Technology. 8th Edition, 2006. Wissenschaftliche Verlagsgesellschaft mbH Stuttgart).

Depending on the embodiment according to the invention and desired purpose, mixtures according to the invention (as described above) can also contain one or more of the components mentioned above in connection with preparations according to the invention.

INDUSTRIAL APPLICATION

A further aspect of the present invention relates to a compound, a salt, a mixture or a preparation, as respectively described or defined above, for use in a method for the treatment of animal or human skin which requires treatment with anti-inflammatory active substances. Regarding the selection of the compounds or the salts and the preferable composition of the mixtures and preparations, the aforesaid respectively applies.

As described above, one aspect of the present invention relates in particular to a preparation used in food and beverage preparations, cosmetic preparations and pharmaceutical preparations (oral consumables), in particular a preparation suitable for the treatment, protection and/or care of the mucous skin and especially of the oral cavity (in particular of the gingiva and the teeth), or a pharmaceutical preparation, for the treatment of inflammatory states of the body of warm-blooded animals. As regards the composition of such a preparation, reference is essentially made to the above explanations.

Preparations according to the invention, in particular preparations according to the invention used for food or enjoyment, in the context of the present invention can in particular be embodied as compositions suitable for consumption (as described below). The preparations used for food or enjoyment in the sense of the present invention can also be used as semi-finished goods for the production of further preparations used for food or enjoyment.

The preparations according to the invention used for food or enjoyment and corresponding semifinished goods and preparations or compositions suitable for consumption are as a rule products which are intended to be introduced into the human oral cavity, to remain there for a certain time and then either be consumed (e.g. ready-to-eat foods, see below) or removed again from the oral cavity (e.g. chewing gums). Thus these products include all articles or substances which are intended to be ingested by people, in the processed, partially processed or unprocessed state. In particular, compositions suitable for consumption are articles which products which are added to foods during the production, processing or modification thereof and are intended to be introduced into the human oral cavity, in particular with the said food. Accordingly, such compositions can in turn be contained in (further) ready-to-use or ready-to-eat preparations used for food or enjoyment (in the context of the present text, ready-to-use or ready-to-eat preparations used for food or enjoyment are in particular foods, especially ready-to-eat foods (see below)). In addition, such compositions can be a component of a semifinished product which optionally can in turn be used for the production of ready-to-use or ready-to-eat preparations used for food or enjoyment.

Preparations used for food or enjoyment in the sense of the present invention are in particular ready-to-use or ready-to-eat preparations, in particular foods, especially ready-to-eat foods, e.g. bakery products (e.g. bread, dry biscuits, cakes, other pastries), confectionery (e.g. chocolates, chocolate bar products, other products in bars, fruit gum, hard and soft caramels, chewing gum), alcoholic or non-alcoholic drinks (e.g. coffee, tea, wine, wine-containing drinks, beer, beer-containing drinks, liqueurs, spirits, brandies, fruit-containing soft drinks, isotonic drinks, refreshment drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or pickled meat products), eggs or egg products (dried egg, egg white, egg yolk), cereal products (e.g. breakfast cereals, muesli bars, prefermented prepared rice products), dairy products (e.g. milk drinks, milk-based ice cream, yoghurt, kefir, cream cheese, soft cheese, hard cheese, dried milk powder, whey, butter, buttermilk, partially or fully hydrolyzed milk protein-containing products), products from soya protein or other soya bean fractions (e.g. soya milk and products prepared therefrom, soya lecithin-containing preparations, fermented products such as tofu or tempe or products prepared therefrom, soya sauces), fruit preparations (e.g. preserves, fruit-flavoured ice cream, fruit sauces, fruit fillings), vegetable preparations (e.g. ketchup, sauces, dried vegetables, deep-frozen vegetables, prefermented vegetables, vegetables marinated in vinegar, preserved vegetables), nibbles (e.g. baked or fried potato crisps or potato dough products, bread dough products, maize- or peanut-based extruded products), fat and oil-based products or emulsions thereof (e.g. mayonnaise, remoulade, dressings, spice preparations), other ready-to-serve meals and soups (e.g. dried soups, instant soups, prefermented soups), spices, spice mixtures and in particular seasonings), which are for example used in the snacks field.

Preferable carrier substances contained in such (preferably spray dried) compositions according to the invention are silicon dioxide (silicic acid, silica gel), carbohydrates and/or carbohydrate polymers (polysaccharides), cyclodextrins, starches, degraded starches (starch hydrolyzates), chemically or physically modified starches, modified celluloses, gum Arabic, ghatti gum, tragacanth, karaya, carrageenan, guar gum, carob flour, alginates, pectin, inulin or xanthan gum.

Preferable starch hydrolysates are maltodextrins and dextrins, where here again maltodextrins with DE values in the range 5 to 20 are particularly preferable. Here it is unimportant what plant originally provided the starch for the production of the starch hydrolyzates. Maize-based starches and starches from tapioca, rice, wheat or potatoes in particular are suitable and readily available. Here previously described carrier substances (e.g. silicon dio-ide) can advantageously function as free-flow agents.

The preparations according to the invention, which as well as one or more compounds of the formula (I), respectively formula (Ia), (Ib), (Ia'), (Ia") and (Ib') and/or salts thereof or a suitable mixture also contain one or more solid carrier substances can for example be produced by mechanical mixing processes, wherein at the same time a comminution of the particles can take place, or by means of spray-drying. As described above, compositions according to the invention which contain solid carrier substances and are produced by means of spray-drying are preferable; concerning the spray-drying, reference is made to U.S. Pat. Nos. 3,159,585, 3,971,852, 4,532,145 or 5,124,162.

Preferable preparations containing carrier substances (as described above) which have been produced by means of spray-drying preferably have a mean particle size in the range from 30 to 300 µm and preferably a residual moisture content of 5 wt. % or less.

According to one embodiment of the present invention, the weight ratio of the total mass of compounds of the formula (I), respectively formula (Ia), (Ib), (Ia'), (Ia") and (Ib') and salts thereof in a preparation described herein containing one or more (suitable for consumption, solid) carrier substances (as described above) to the total mass of (suitable for consumption, solid) carrier substances preferably lies in the range from 1:10 to 1:100000, preferably in the range from 1:50 (preferably from 1:100) to 1:20000, particularly preferably in the range from 1:100 (preferably from 1:1000) to 1:5000, based on the dry mass of the preparation.

In a preparation (as described above) containing one or more (suitable for consumption, solid) carrier substances (as described above), the proportion of the total quantity of compounds of the formula (I), salts thereof and (suitable for consumption, solid) carrier substances, based on the total weight of the preparation, preferably lies in the range from 70 to 100 wt. %, preferably in the range from 85 to 100 wt. %.

The preparations according to the invention used for food or enjoyment, as well as normally used animal or plant raw materials, can additionally contain water, squalane or squalene, natural oils (e.g. olive oil, sunflower oil, soya oil, peanut oil, rape oil, almond oil, palm oil, coconut oil, palm nut oil, borage seed oil and more of the like), natural ester oils (e.g. jojoba oil), fats, waxes and other natural fatty substances, carbohydrates, for example glucose, sucrose or lactose, sweeteners, for example aspartame, cyclamate, saccharin, xylitol or sorbitol, bitter substances, for example caffeine or quinine, bitterness-suppressing substances, for example lactisol, flavour-intensifying substances, for example sodium glutamate or inositol phosphate, amino acids, for example glycine, alanine, leucine, isoleucine, valine, proline, lysine, asparagine, aspartic acid, glutamine, glutamic acid, tryptophan, phenylalanine, tyro-sine, threonine, serine, cystine, cysteine, methionine, hydroxyproline, arginine or histidine, peptides, proteins, enzymes, fruit acids, preferably lactic acid, malic acid or citric acid, as well as emulsifiers, which can advantageously be selected from the group of the ionic, nonionic, polymeric, phosphate-containing and zwitterionic emulsifiers, and in particular one or more thickeners, which can advantageously be selected from the group of the poly-saccharides or derivatives thereof, e.g. hyaluronic acid, guar gum, carob flour, xanthan gum or cellulose derivatives, and natural, nature-identical or synthetic aromas and salts, for ex-ample sodium chloride or potassium chloride.

The cosmetic and pharmaceutical preparations, which are preferably dermatological preparations according to the invention can contain cosmetic auxiliary agents and/or additives such as are normally used in such preparations, e.g. sunscreens (e.g. organic or inorganic light filter substances, preferably micropigments), preservatives, bactericides, fungicides, virucides, cooling active substances, plant extracts, inflammation-inhibiting active substances, wound healing accelerating substances (e.g. chitin or chitosan and derivatives thereof), film-forming substances (e.g. polyvinylpyrrolidones or chitosan or derivatives thereof), common antioxidants, vitamins (e.g. vitamin C and deriva-tives, tocopherols and derivatives, vitamin A and derivatives), 2-hydroxycarboxylic acids (e.g. citric acid, malic acid, L-, D-, or dl-lactic acid), skin lighteners (e.g. kojic acid, hydroquinone or arbutin), skin colorants (e.g. walnut extracts or dihydroxyacetone), perfumes, substances for prevention of foaming, colorants, pigments which have a colorant action, thickeners, surfactant substances, emulsifiers, plasticizing, moistening and/or humectant substances (e.g. glycerine or urea), fats, oils, unsaturated fatty acids or derivatives thereof (e.g. linolic acid, alphalinolenic acid, gamma-linolenic acid or arachidonic acid and their respective natural or synthetic esters), waxes or other normal components of a cosmetic or dermatological formulation such as alcohols, polyols, polymers, foam stabilizers, electrolytes, organic solvents, silicone derivatives or chelating agents (e.g. ethylendiaminetetraacetic acid and derivatives).

The particular quantities to be used can easily be determined by those skilled in the art by simple testing, depending on the nature of the particular product.

Preferably preparations according to the invention (as described above) additionally contain one or more antioxidants, where the antioxidant or antioxidants is/are not a compound or compounds of the formula (I) or a salt thereof. In particular, as such antioxidants, all antioxidants suitable or usual for the respective use can be used. The antioxidant or antioxidants is or are preferably selected from the group consisting of amino acids (e.g. glycine, histidine, 3,4-dihydroxyphenylalanine, tyrosine, tryptophan) and derivatives thereof, imidazoles (e.g. urocanic acid) and derivatives thereof, peptides (D,L-carnosine, D-carnosine, L-carnosine, anserine) and derivatives thereof, carotenoids, carotenes (e.g. beta-carotene, alpha-carotene, lycopene) and derivatives thereof, chlorogenic acid and derivatives thereof, lipoic acid and derivatives thereof, aurothioglucose, propylthiouracil and other thiols (e.g. thiore-doxin, glutathione, cysteine, cystine, cystamine and glycosyl and N-acyl derivatives thereof or alkyl esters thereof) and salts thereof, dilauryl thiodipropionate, distearyl thiodipropionate, thiodipropionic acid and derivatives thereof and phenolic acid amides of phenolic benzylamines (e.g. homovanillic acid, 3,4-dihydroxyphenylacetic acid, ferulic acid, sinapinic acid, caffeic acid, dihydroferulic acid, dihydrocaffeic acid, vanillomandelic acid- or 3,4-dihydroxymandelic acid amides of 3,4-dihydroxybenzyl, 2,3,4-trihydroxybenzyl- or 3,4,5-trihydroxybenzyl-amine), catechol oximes or catechol oxime ethers (e.g. 3,4-dihydroxybenzaldoxime or 3,4-dihydroxybenzaldehyde O-ethyloxime), also (metal) chelators (e.g. 2-hydroxyfatty acids, phytic acid, lactoferrin), humic acid, bile acids, bile extracts, bilirubin, biliverdin, folic acid and derivatives thereof, ubiquinone and ubiquinol and derivatives thereof, vitamin C and derivatives thereof (e.g. ascorbyl palmitate, magnesium ascorbyl phosphate, ascorbyl acetate), tocopherols and derivatives (e.g. alpha-tocopherol, vitamin E acetate), vitamin A and derivatives (e.g. vitamin A palmitate), rutinic acid and derivatives thereof, flavonoids (e.g. quercetin, alpha-glucosylrutin) and derivatives thereof, phenolic acids (e.g. gallic acid, ferulic acid) and derivatives thereof (e.g. gallic acid propyl ester, ethyl ester and octyl ester), furfurylideneglucitol, dibutylhydroxytoluene, butylhydroxyanisole, uric acid and derivatives thereof, mannose and derivatives thereof, zinc and derivatives thereof (e.g. ZnO, ZnSO4), selenium and derivatives thereof (e.g. selenomethionine), stilbene and derivatives thereof (e.g. stilbene oxide, resveratrol) and the derivatives of these named (active) substances suitable in the context of the present invention.

The (pharmaceutical) preparations in the sense of the present invention used for the treatment of inflammatory states of warm-blooded animals can also be used as semi-finished goods for the production of further pharmaceutical preparations used for the treatment of inflammatory states of warm-blooded animals.

The pharmaceutical preparations according to the invention used for the treatment of inflammatory states of warm-blooded animals, and corresponding semi-finished goods are as a rule products which are intended to be introduced into the body of warm-blooded animals or used on the body of warm-blooded animals.

The pharmaceutical preparations according to the invention used for the treatment of inflammatory states of warm-blooded animals in the sense of the present invention are preferably ready-to-use preparations, in particular medicaments and medicinal products, preferably in the following forms: solid galenical forms (such as for example tablets (with and without coating, with and without modified release), sugar-coated tablets (with and without coating, with and without modified release), capsules (soft or hard gelatine capsules with and without modified release) granules (with and without modified release), powders (with and without modified release), suppositories (with and without coating, with and without modified release) lozenges and chewing gums), and liquid forms (such as for example solutions, suspensions, emulsions, syrups (colloquially cough syrup), mouthwashes, gargle solutions, throat sprays or nasal sprays, nasal drops, nasal rinse solutions, nasal powders, nasal ointments or ear drops, ear sprays, ear rinse solutions, ear powders and aural tampons), and semisolid forms (such as for example hydrophobic ointments including for example: hydrocarbon gels, lipogels, silicone gels, oleogels and water-absorbing ointments including for example absorption bases, hydrophilic ointments, hydrophilic gels (hydrogels) or pastes, and inhalants (such as for example compressed gas dispenser inhalers, powder inhalers, inhalers with atomisers, and inhalation concentrates for the preparation of inhalations), and active substance-containing plasters or other therapeutic systems.

The pharmaceutical preparations according to the invention can contain (further) pharmaceutical auxiliary and/or additive substances, such as are normally used in such preparations, e.g. active substances from the group of the non-steroidal anti-inflammatories, anti-biotics, systemically active steroids, anti-TNF-alpha antibodies or other biotechnologically produced active substances and/or pure substances such as budesonide, sulfasalazine, azathioprine/6-mercaptopurine or methotrexate. And for example fillers (e.g. cellulose, calcium carbonate), free-flow and anticaking agents (e.g. talc, magnesium stearate), coatings (e.g. polyvinyl acetate phthalate, hydroxypropyl-methylcellulose phthalate), disintegrants (e.g. starch, crosslinked polyvinylpyrrolidone), plasticizers (e.g. triethyl citrate, dibutyl phthalate) substances for granulation (lactose, gelatine), retardation (e.g. poly(meth)acrylic acid methyl/ethyl/2-trimethylaminoethyl ester copolymers in dispersion, vinyl acetate/crotonic acid copolymers) and compacting (e.g. microcrystalline cellulose, lactose), solvent, suspension or dispersion agents (e.g. water, ethanol), emulsifiers (e.g. cetyl alcohol, lecithin), substances for modification of the rheological properties (silicon dioxide, sodium alginate), substances for microbial stabilization (e.g. benzalkonium chloride, potassium sorbate), preservatives and antioxidants (e.g. DL-alpha-tocopherol, ascorbic acid), substances for modification of the pH (lactic acid, citric acid), propellant or inert gases (e.g. fluorinated chlorohydrocarbons, carbon dioxide), colorants (iron oxides, titanium dioxide), ointment bases (e.g. paraffins, beeswax), inter alia as described in the technical literature (e.g. Schmidt, Christin. Active and Auxiliary Substances for Individual and Bulk Formulation, and Large-scale Manufacture. 1999; Wissenschaftliche Verlagsgesellschaft mbH Stuttgart or Bauer, Frömming Führer. Textbook of Pharmaceutical Technology. 8th Edition, 2006. Wissenschaftliche Verlagsgesellschaft mbH Stuttgart).

Preferable solvents according to the present invention represent ternary mixtures of certain 1,2-alkandiols, certain aliphatic alcohols and water.
- (i) 1,2-Alkandiols. Suitable 1,2-alkandiols encompass 1,2-butadiol, 1,2-pentandiol, 1,2-hexandiol, 1,2-heptanddiol, 1,2-octandiol, 1,2-nonandiol, 1,2-decandiol, 1,2-undecandiol, 1,2,dodecandiol and their mixtures. The preferred 1,2-alkandiol is 1,2-pentandiol.
- (ii) Aliphatic alcohols. Suitable aliphatic alcohols are selected from the group consisting of ethanol, n-propanol, isopropylalcohol, the isomeric butanols and their mixtures. The preferred species is ethanol, in particular with a purity of at least 95%.

Overall preferred are solvent mixtures wherein the 1,2-alkandiol is 1,2-pentandiol and the aliphatic alcohol is ethanol.

The particular quantities to be used can easily be determined by those skilled in the art by simple testing, depending on the nature of the particular product.

A pharmaceutical composition in the sense of the present invention comprise (a) about 1.0 to about 10.0% b.w., preferably about 2.0 to about 8.0% b.w. and more preferably about 2.5 to about 5.0% b.w. of at least one compounds of the formula (I), respectively formula (Ia), (Ib), (Ia'), (Ia") and (Ib') and/or salts thereof, (b) about 15 to about 50% b.w., preferably about 20 to about 40% b.w. and more preferably about 25 to about 35% b.w. of at least 1,2-alkandiol having 4 to 12 carbon atoms; and;

(c) about 15 to about 25% b.w., preferably about 20 to about 22% b.w. of at least one aliphatic alcohol having 2 to 4 carbon atoms, on condition that the amounts add with water to give 100%.

The compositions are suitable for topical or oral application. They may represent a cream, a gel, a lotion, an ointment, a powder, a tablet, or a capsule.

According to one aspect of the present invention, a preparation according to the invention wherein the proportion of the total quantity of compounds of the formula (I), respectively formula (Ia), (Ib), (Ia'), (Ia") and (Ib') and salts thereof in the preparation lies in the range from 0.0001 to 30 wt. %, preferably in the range from 0.001 to 20 wt. %, and particularly preferably in the range from 0.001 to 5 wt. %, based on the total weight of the preparation, is preferable.

According to a preferable embodiment of the present invention, the extracts or mixtures described herein are incorporated in the form of emulsions into liposomes, for example starting from phosphatidylcholine, into microspheres, into nanospheres or also into capsules, granules or extrudates, for example of starch, starch derivatives, cellulose or cellulose derivatives (for example hydroxypropylcellulose), other polysaccharides (for example alginates), natural fats, natural waxes (for example beeswax, carnauba wax) or of proteins, for example gelatine.

In connection with the present invention, a prophylactic and/or therapeutic method as described above, with the following step, is also described: contacting of (human or animal) tissue and/or of the (human or animal) cells with an inflammation-inhibiting effective quantity of a compound of the formula (I), respectively formula (Ia), (Ib), (Ia'), (Ia") and (Ib') or a salt thereof, as respectively described above, or of a preparation as described above.

The contacting of the tissue or the cells with one or more compounds of the formula (I), respectively formula (Ia), (Ib), (Ia'), (Ia") and (Ib') and/or salts thereof or a mixture or preparation according to the invention (as respectively described above) here—depending on the tissue to be treated or the cells to be treated—can also be effected by external (e.g. topical) or internal use (e.g. oral application).

The following examples serve to clarify the invention, without thereby restricting it.

EXAMPLES

Formulation Examples

The following tables show formulation examples comprising the products of the present invention All amounts are in % b.w.

TABLE I

| Sugar-free hard caramels (amounts in % b.w.) | | |
|---|---|---|
| Ingredient | A | B |
| Palatinit, type M | Ad 100 | |
| Water | 24.82 | 24.82 |
| Peppermint flavour | 0.15 | 0.05 |
| Hesperetin | 0.10 | |
| Trans-pellitorin (10% in ethanol) | 0.01 | |
| Compound 7 | 0.0025 | |
| Compound 5 | 0.001 | 0.001 |

Palatinit was mixed with water and the mixture was melted at 165° C. then cooled to 115° C. Flavouring and extract produced according to the invention, and trans-pellitorin in case A and hesperetin in case B, were added, and after thorough mixing poured into moulds, and after solidification removed from the foil and then individually packed.

TABLE II

| Chewing gum for bad breath | | | | |
|---|---|---|---|---|
| Ingredients | A | B | C | D |
| Chewing gum base | 21.00 | 21.00 | 21.00 | 21.00 |
| Glucose syrup | 16.80 | 16.80 | 16.50 | 16.50 |
| Glycerine | 0.50 | 0.50 | 0.50 | 0.50 |
| Sugar powder | 60.00 | 60.00 | 60.40 | 60.40 |
| Spearmint flavour | 1.50 | 1.50 | 1.50 | 1.50 |
| Compound 1 | 0.003 | | | |
| Compound 2 | | 0.0025 | | 0.0025 |
| Compound 3 | | | 0.002 | 0.002 |
| Compound 6 | 0.001 | 0.001 | 0.0015 | |

TABLE III

| Sugar-free chewing gum for bad breath | | | | |
|---|---|---|---|---|
| Ingredients | A | B | C | D |
| Chewing gum base | 30.00 | 30.00 | 30.00 | 30.00 |
| Sorbitol, powder | 38.25 | 38.25 | 38.40 | 38.40 |
| Palatinit | 9.50 | 9.50 | 9.50 | 9.50 |
| Xylitol | 2.00 | 2.00 | 2.00 | 2.00 |
| Mannitol | 3.00 | 3.00 | 3.00 | 3.00 |
| Aspartame | 0.10 | 0.10 | 0.10 | 0.10 |
| Acesulfam K | 0.10 | 0.10 | 0.10 | 0.10 |
| Emulgum/emulsifier | 0.30 | 0.30 | 0.30 | 0.30 |
| Sorbitol 70%, in water | 14.00 | 14.00 | 14.00 | 14.00 |
| Glycerine | 1.00 | 1.00 | 1.00 | 1.00 |
| Cinnamon/menthol flavour | 1.50 | 1.50 | 1.50 | 1.50 |
| Compound 4 | 0.002 | | 0.001 | |
| Compound 8 | 0.003 | | | |
| Compound 5 | | 0.0015 | 0.001 | 0.002 |
| Compound 7 | | 0.002 | | |

TABLE IV

| Ready-to-use mouthwash solution with fluoride for bad breath | | | |
|---|---|---|---|
| Ingredients | A | B | C |
| Ethanol | 7.00 | 7.00 | 7.00 |
| Glycerine | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Compound 5 | 0.0015 | 0.001 | 0.001 |

TABLE IV-continued

Ready-to-use mouthwash solution with fluoride for bad breath

| Ingredients | A | B | C |
|---|---|---|---|
| Compound 8 |  | 0.002 |  |
| Compound 7 |  |  | 0.0015 |
| Colorant | 0.01 | 0.01 | 0.01 |
| Dist. water |  | Ad 100 |  |

TABLE V

Mouthwash solution (concentrate) for bad breath

| Ingredients | A | B | C |
|---|---|---|---|
| Ethanol, 95% | 80.00 | 80.00 | 80.00 |
| Na cyclamate | 0.15 | 0.15 | 0.15 |
| Eucalyptus/wintergreen flavour | 3.50 | 3.50 | 3.50 |
| Colorant | 0.01 | 0.01 | 0.01 |
| Compound 1 | 0.003 |  | 0.002 |
| Compound 4 |  | 0.003 |  |
| Compound 6 |  |  | 0.002 |
| Demin. water |  | Ad 100 |  |

TABLE VI

Mouthwash solution with fluoride for bad breath

| Ingredient | INCI | A |
|---|---|---|
| Ethyl alcohol | Ethyl alcohol | 10.00 |
| Cremophor CO 40 | Cremophor CO 40 (PEG 40 hydrogenated castor oil) | 1.00 |
| Benzoic acid | Benzoic acid | 0.12 |
| Aroma (PF1, PF2, PF3 or PF4) | Flavour | 0.25 |
| Demin. water | Water (deionized) | 83.28 |
| Sorbitol 70% | Sorbitol 70% | 5.00 |
| Sodium saccharin | Sodium saccharin 450 | 0.07 |
| Sodium fluoride | Sodium fluoride | 0.18 |
| Compound 5 |  | 0.002 |

TABLE VII

Toothpaste

| Ingredient | INCI | A |
|---|---|---|
| Demin. water | Water (deionized) | 26.31 |
| Sorbitol 70% | Sorbitol 70% | 70.0 |
| Solbrol M (Na salt) | Solbrol M (Sodium salt) (methylparaben) | 0.15 |
| Trisodium phosphate | Trisodium phosphate | 0.10 |
| Saccharin | Saccharin | 0.20 |
| Sodium monofluorophosphate | Sodium monofluorophosphate | 1.14 |
| PEG 1500 | PEG 1500 | 5.00 |
| Sident 9 (abrasive silica gel) | Sident 9 (abrasive silica) | 10.00 |
| Sident 22 S (thickener) | Sident 22 S (thickening silica) | 8.00 |
| Sodium carboxymethylcellulose | Sodium carboxymethylcellulose | 1.10 |
| Titanium (IV) oxide | Titanium (IV) oxide | 0.50 |
| Sodium laurylsulphate (SLS) | Sodium laurylsulphate (SLS) | 1.50 |
| Aroma (PF1, PF2, PF3 or PF4) | Flavour | 1.00 |
| Compound 5 |  | 0.0025 |

TABLE VIII

Anti-plaque toothpaste

| Ingredient | A | B |
|---|---|---|
| Carrageenan | 0.90 | 0.90 |
| Glycerol | 15.00 | 15.00 |
| Sorbitol 70%, in water | 25.00 | 25.00 |
| PEG 1000 | 3.00 | 3.00 |
| Na fluoride | 0.24 | 0.24 |
| Tetrapotassium diphosphate | 4.50 | 4.50 |
| Tetrasodium diphosphate | 1.50 | 1.50 |
| Na saccharinate | 0.40 | 0.40 |
| Precipit. silica gel | 20.00 | 20.00 |
| Titanium dioxide | 1.00 | 1.00 |
| Triclosan | 0.30 | 0.30 |
| PHB methyl ester | 0.10 | 0.10 |
| Spearmint flavour (containing 60 wt.% L-carvone and 25 wt.% L-menthol) | 1.00 | 1.20 |
| Compound 3 | 0.0025 | — |
| Compound 8 | — | 0.003 |
| Sodium dodecylsulphate | 1.30 | 1.30 |
| Demin. water | Ad 100 |  |

TABLE IX

Tooth cream for pain-sensitive teeth

| Ingredient | A | B |
|---|---|---|
| Na carboxymethylcellulose | 0.70 | 0.70 |
| Xanthan gum | 0.50 | 0.50 |
| Glycerol | 15.00 | 15.00 |
| Sorbitol 70%, in water | 12.00 | 12.00 |
| Potassium nitrate | 5.00 | 5.00 |
| Sodium monofluorophosphate | 0.80 | 0.80 |
| PHB methyl ester | 0.15 | 0.15 |
| PHB propyl ester | 0.05 | 0.05 |
| Na saccharinate | 0.20 | 0.20 |
| Flavour (PF1, PF2, PF3 or PF4) | 1.00 | 1.00 |
| Compound 4 | 0.003 | — |
| Compound 5 | — | 0.002 |
| Ca carbonate | 35.00 | 35.00 |
| Silicon dioxide | 1.00 | 1.00 |
| Sodium dodecylsulphate (SDS) | 1.50 | 1.50 |
| Demin. water | Ad 100 |  |

TABLE X

Gelatine capsules for bad breath for direct consumption

|  | Ingredients | A | B | C |
|---|---|---|---|---|
| Gelatine casing | Glycerine | 2.014 | 2.014 | 2.014 |
|  | Gelatine 240 Bloom | 7.91 | 7.91 | 7.91 |
|  | Sucralose | 0.065 | 0.065 | 0.065 |
|  | Allura Red | 0.006 | 0.006 | 0.006 |
|  | Brilliant Blue | 0.005 | 0.005 | 0.005 |
| Core filling | Plant oil triglycerides | 82.00 | 74.00 | 60.00 |
|  | Flavour B | 7.9 | 15.50 | 29.5 |
|  | Compound 1 | 0.001 | 0.002 | — |
|  | Compound 5 | 0.0015 | — | 0.002 |

Flavour B had the following composition (data in weight %): 0.1% neotame (powder), 0.05% aspartame, 29.3% peppermint oil (Avensis), 29.3% peppermint oil (Piperita; Willamette), 2.97% sucralose, 2.28% triacetin, 5.4% diethyl tartrate, 12.1% peppermint oil (Yakima), 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, has a diameter of 5 mm; the weight ratio between core and casing material is about 90:10. The capsules open in the mouth in less than 10 secs, and dissolve completely within 50 secs.

TABLE XI

Capsules

| Ingredient | A | B |
|---|---|---|
| Magnesium stearate | 0.5 | 0.5 |
| Sucralose | 0.025 | 0.025 |
| Sorbitol Powder | to 100 | to 100 |
| Compound 5 | 0.002 | |
| Compound 7 | | 0.003 |

Test Studies

Example TS1

Anti-inflammatory action in human gingival fibroblastic cells (HGF-1)

Human gingival fibroblastic cells (HGF-1) were sowed out in 24-well plates with 15,000 cells per well and cultivated for 3 to 5 days. DMEM containing 10% FBS, 1% penicillin/streptomycin and 4% glutamine was used as the medium. For determination of the anti-inflammatory action the cells were incubated with 10 µg/ml PG-LPS for 6 hrs. Subsequently, the release of IL-8 was determined per magnetic bead (Procarta, Affimetrix) using a MAGPIX equipment (Merck-Millipore) and analysed using the Milliplex software (Merck Millipore). In each case 4 samples with two technical replicates were measured. In addition to this control the cells were co-incubated with
(a) 10 µg/ml PG-LPS and also with
(b) solutions of the compounds 1-8, resulting in final compound concentration of 1 µM or 100 µM, respectively, in the assay.

After incubation the cell culture medium was transferred into an Eppendorf reaction vessel and at 4° C. for 10 min subjected to centrifugation (1000×g) in order to separate the cell debris. The supernatant was stored at −80° C. until analysis. The results of the release of IL-8 after 9 hrs are shown in Table 1a. Data are displayed as % IL-8 release vs PG-LPS control (% T/C).

TABLE 1a

Release of IL-8 by HGF-1 cells 6 h after stimulation with 10 µg/ml PG-LPS or respectively co-incubation with compounds 1-8. Data are displayed as % IL-8 release vs PG-LPS control (% T/C).

| | 1 µM Test Compound | | 100 µM Test Compound | |
|---|---|---|---|---|
| Test Compound | IL-8 T/C [%] | IL-8 Standard Deviation | IL-8 T/C [%] | IL-8 Standard Deviation |
| 10 µg/ml LPS control – 6 h | 100.00 | 19.146 | 100.00 | 22.043 |
| 10 µg/ml LPS + Compound 1 | 89.87 | 25.49 | 60.72 | 12.07 |
| 10 µg/ml LPS + Compound 2 | 48.84 | 12.76 | 65.76 | 10.88 |
| 10 µg/ml LPS + Compound 3 | 47.63 | 6.08 | 63.37 | 11.56 |
| 10 µg/ml LPS + Compound 4 | 106.46 | 12.86 | 50.01 | 8.21 |
| 10 µg/ml LPS + Compound 5 | 60.30 | 13.86 | 4.53 | 0.30 |
| 10 µg/ml LPS + Compound 6 | 96.38 | 44.42 | 44.16 | 12.19 |
| 10 µg/ml LPS + Compound 7 | 61.73 | 6.25 | 31.31 | 3.19 |
| 10 µg/ml LPS + Compound 8 | 88.30 | 29.66 | 58.95 | 7.81 |

The invention claimed is:

1. A method for reducing the release of interleukin-8 (IL-8) in the treatment of inflammation comprising administering to a human or an animal in need thereof compound (5), or a salt thereof

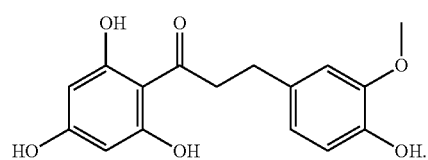

(5)

2. The method of claim 1, wherein said inflammation is inflammation of gingiva and comprises administering a therapeutically effective amount of the compound (5) or salt thereof to an oral mucosa.

* * * * *